US009168408B2

(12) United States Patent
Shtarov et al.

(10) Patent No.: US 9,168,408 B2
(45) Date of Patent: Oct. 27, 2015

(54) SURFACTANT COMPOSITION FROM POLYFLUOROALKYLSULFONAMIDO ALKYL AMINES

(75) Inventors: Alexander Borisovich Shtarov, Wilmington, DE (US); Volodymyr B. Pashovych, Bristol, CT (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 1261 days.

(21) Appl. No.: 13/048,278

(22) Filed: Mar. 15, 2011

(65) Prior Publication Data

US 2011/0232924 A1 Sep. 29, 2011

Related U.S. Application Data

(60) Provisional application No. 61/317,473, filed on Mar. 25, 2010.

(51) Int. Cl.
*A62D 1/02* (2006.01)
*A62D 1/00* (2006.01)
*C07C 311/09* (2006.01)
*C07C 311/24* (2006.01)
*C11D 1/00* (2006.01)

(52) U.S. Cl.
CPC ............ *A62D 1/0071* (2013.01); *A62D 1/0035* (2013.01); *C07C 311/09* (2013.01); *C07C 311/24* (2013.01); *C11D 1/004* (2013.01)

(58) Field of Classification Search
CPC .. C07C 309/15; C07C 311/09; C07C 311/24; A62D 1/0085; A62D 1/0071; A62D 1/0035; C11D 1/004
USPC .................. 516/9, 12; 252/2, 3, 8.05; 562/113
See application file for complete search history.

(56) References Cited

U.S. PATENT DOCUMENTS

| 3,708,538 | A | | 1/1973 | Hahn et al. |
|---|---|---|---|---|
| 3,721,706 | A | | 3/1973 | Hoffmann et al. |
| 4,069,158 | A | | 1/1978 | Bertocchio et al. |
| 4,296,034 | A | | 10/1981 | Bouvet et al. |
| 4,383,929 | A | * | 5/1983 | Bertocchio et al. .......... 252/8.05 |
| 4,424,133 | A | | 1/1984 | Mulligan |
| 4,431,595 | A | | 2/1984 | Hashimoto et al. |
| 4,486,391 | A | | 12/1984 | Hashimoto |
| 4,826,634 | A | | 5/1989 | Baasner et al. |
| 4,836,281 | A | | 6/1989 | Robin et al. |
| 4,921,696 | A | | 5/1990 | VanderMeer et al. |
| 4,983,769 | A | | 1/1991 | Bertocchio et al. |
| 5,085,786 | A | | 2/1992 | Alm et al. |
| 5,144,069 | A | | 9/1992 | Stern et al. |
| 5,399,756 | A | | 3/1995 | Schneider et al. |
| 5,514,493 | A | | 5/1996 | Waddell et al. |
| 5,580,847 | A | | 12/1996 | Morikawa et al. |
| 6,201,122 | B1 | | 3/2001 | Dams |
| 6,960,410 | B2 | | 11/2005 | Kim et al. |

| 2001/0001478 | A1 | | 5/2001 | Dams et al. |
|---|---|---|---|---|
| 2001/0038949 | A1 | | 11/2001 | Hatazaki et al. |
| 2006/0177717 | A1 | | 8/2006 | Teasley et al. |
| 2007/0015937 | A1 | * | 1/2007 | Hintzer et al. ................ 562/586 |
| 2007/0027349 | A1 | | 2/2007 | Brandstadter et al. |
| 2007/0093678 | A1 | | 4/2007 | Umemoto et al. |
| 2007/0161537 | A1 | * | 7/2007 | Boggs et al. .................. 510/475 |
| 2009/0137773 | A1 | | 5/2009 | Jackson et al. |
| 2009/0137831 | A1 | | 5/2009 | Rostovtsev |
| 2010/0003737 | A1 | | 1/2010 | Murphy et al. |

FOREIGN PATENT DOCUMENTS

| CN | 1528479 | A | 9/2004 |
|---|---|---|---|
| DE | 2617746 | A1 | 11/1976 |
| EP | 0073863 | A1 | 9/1981 |
| EP | 1013311 | A1 | 6/2000 |
| EP | 1088814 | A1 | 9/2000 |
| GB | 1378984 | | 10/1972 |
| JP | 1980146173 | A | 11/1980 |
| JP | 1983038569 | A | 3/1983 |
| JP | 1983038570 | A | 3/1983 |
| JP | 1983038571 | A | 3/1983 |
| JP | 58179300 | A * | 10/1983 |
| JP | 1993238705 | A | 9/1993 |
| JP | 1993275406 | A | 10/1993 |
| JP | 1993275407 | A | 10/1993 |
| NL | 7807188 | A | 1/1979 |
| WO | 9746283 | A1 | 12/1997 |
| WO | 9929373 | A1 | 6/1999 |
| WO | 2008083199 | A | 7/2008 |

(Continued)

OTHER PUBLICATIONS

Hawley's Condensed Chemical Dictionary, (2007), John Wiley & Sons, Inc. Online @ http://onlinelibrary.wiley.com/book/10.1002/9780470114735/titles headwords = 168, 324-325, 642, 655-656, 852, and 1186 (downloaded Dec. 15, 2014), pp. 1-3.*

Derwent Abstract, week 199001, London: Derwent Publications Ltd., AN 1983-829589, Class A60, JP 58-179300 A, (Dianippon Ink & Chem KK), abstract, pp. 1-3.*

Abstract on Espacenet—Bibliographic data, CN1957078—May 2, 2007, (PCBU Services Inc), abstract, pp. 1-2, online @ http://worldwide.espacenet.com/?locale=EN_ep, (downloaded Feb. 26, 2015, Patent Family includes US 20070161537 A).*

(Continued)

*Primary Examiner* — Daniel S Metzmaier

(57) ABSTRACT

The present invention relates to aminosulfonate and aminocarboxylate compositions derived from a mixture of polyfluoroalkylsulfonamido alkyl amines including at least one polyfluoroalkylsulfonamido alkyl amine and its analog, a di(polyfluoroalkylsulfonamido alkyl) amine. The aminosulfonate and aminocarboxylate compositions are useful for many purposes including amphoteric surface-active agents and aqueous film forming foams in fire fighting applications.

14 Claims, No Drawings

(56) References Cited

FOREIGN PATENT DOCUMENTS

| WO | 2008089391 A1 | 7/2008 |
|----|---------------|--------|
| WO | 2011046793 A1 | 4/2011 |
| WO | 2011046795 A1 | 4/2011 |

OTHER PUBLICATIONS

Abstract on Espacenet—Bibliographic data, CN101312943—Nov. 26, 2008, (3M Innovative Properties Co), abstract, pp. 1, online @ http://worldwide.espacenet.com/?locale=EN_ep,(downloaded Feb. 26, 2015,Patent Family includes US 20070015937 A).*

Abstract on Espacenet—Bibliographic data, CN1743062—Mar. 8, 2006, (Nanjing Polytechnique Univ), abstract, pp. 1, online @ http://worldwide.espacenet.com/?locale=EN_ep, (downloaded Feb. 26, 2015).*

JPO on EAST, Patent Abstracts of Japan, Japan patent Office, Tokyo, Japan, JP 59046252 A (Mar. 1984), Abstract.*

International Search Report and The Written Opinion of the International Searching Authority, PCT/US2011/029351, dated Jun. 29, 2011.

Reagen et al., Analytical Techniques and Method Validation for the Measurement of Selected Semivolatile and Nonvolatile Organofluorochemicals in Air, Journal of Occupational and Environmental Hygiene, taylor and Francis, Philadelphia, PA 2004, 559-569.

Benfodda et al., A convenient sysnthesis of N-functionalized perfluoroalkanesulfonamides, Phosphorus, sulfuf and Silicon and the related elements, Taylor and Francis, US, 185, 9, 2010, 1905-1914.

\* cited by examiner

SURFACTANT COMPOSITION FROM POLYFLUOROALKYLSULFONAMIDO ALKYL AMINES

FIELD OF THE INVENTION

The present invention relates to aminosulfonates and aminocarboxylates derived from a mixture of polyfluoroalkylsulfonamido alkyl amines including at least one polyfluoroalkylsulfonamido alkyl amine and its analog, a di(polyfluoroalkylsulfonamido alkyl) amine.

BACKGROUND OF THE INVENTION

Aminosulfonates and aminocarboxylates are conventionally made from polyfluoroalkylsulfonamido alkyl amines which are subjected to N-alkylation with haloalkyl substituted reagents as described in U.S. Pat. No. 4,431,595 and Japanese Publication No. JP59046252. Such aminosulfonates and aminocarboxylates are useful for a variety of purposes and can be particularly useful as amphoteric surface-active agents, and are in particular suitable for fire fighting applications.

BRIEF SUMMARY OF THE INVENTION

Conventionally, aminosulfonates and aminocarboxylates are made from a polyfluoroalkylsulfonamido alkyl amine without its di(polyfluoroalkylsulfonamido alkyl) amine analog. In contrast, the present invention provides a method of making aminosulfonates and aminocarboxylates from a mixture of amines comprising at least one polyfluoroalkylsulfonamido alkyl amine and its analog, a di(polyfluoroalkylsulfonamido alkyl) amine. In has now been discovered that the di(polyfluoroalkylsulfonamido alkyl) amine analog imparts superior surfactant properties in aminosulfonates and aminocarboxylates manufactured therefrom. Conversely, use of a polyfluoroalkylsulfonamido alkyl amine without its di(polyfluoroalkylsulfonamido alkyl) amine analog results in poorer surfactant properties in aminosulfonates and aminocarboxylates manufactured therefrom.

Accordingly, the aminosulfonates and aminocarboxylates of the present invention are made from a mixture of amines comprising:
i) at least one polyfluoroalkylsulfonamido alkyl amine represented by

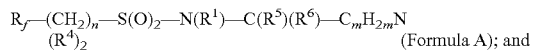

$R_f$—$(CH_2)_n$—$S(O)_2$—$N(R^1)$—$C(R^5)(R^6)$—$C_mH_{2m}N(R^4)_2$ (Formula A); and ii) at least one di(polyfluoroalkylsulfonamido alkyl) analog of i) as represented by

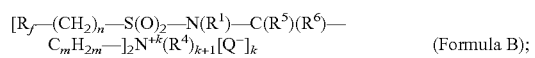

$[R_f$—$(CH_2)_n$—$S(O)_2$—$N(R^1)$—$C(R^5)(R^6)$—$C_mH_{2m}$—$]_2N^{+k}(R^4)_{k+1}[Q^-]_k$ (Formula B);

wherein:
Q is a monovalent anion preferably chosen from halogen, alkylcarboxylate, alkylsulfonate, and more preferably halogen;
k is 0 or 1;
each $R_f$ is the same in i) and ii) and chosen from a $C_2$-$C_{12}$ polyfluoroalkyl, comprising partially of completely fluorinated linear or branched alkyl, optionally interrupted by one to four groups chosen from: —O—, —S—, —S(O)—, and —$S(O)_2$—;
each n in i) and ii) is the same and chosen from an integer from 0 to 6;
each m in i) and ii) is the same and chosen from an integer from 0 to 10;
each $R^1$, $R^5$, $R^6$ is independently chosen from hydrogen, $C_1$ to $C_6$ hydroxyalkyl, $C_1$ to $C_6$ halogen substituted alkyl, or a $C_1$ to $C_6$ linear or branched alkyl; provided that each $R^1$ in i) and ii) are the same, each $R^5$ in i) and ii) are the same, and each $R^6$ in i) and ii) are the same;
each $R^4$ in i) and ii) are the same and chosen from hydrogen or a $C_1$ to $C_6$ alkyl, preferably hydrogen.

A mixture of amines comprising a polyfluoroalkylsulfonamido alkyl amines (Formula A) and its di(polyfluoroalkylsulfonamido alkyl) amine analog (Formula B) are subjected to N-alkylation thereby producing the aminosulfonate and aminocarboxylate compositions of the invention which comprises:
i) at least one compound represented by

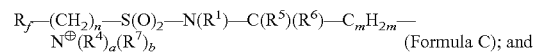

$R_f$—$(CH_2)_n$—$S(O)_2$—$N(R^1)$—$C(R^5)(R^6)$—$C_mH_{2m}$—$N^{\oplus}(R^4)_a(R^7)_b$ (Formula C); and ii) at least one compound represented by

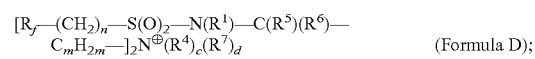

$[R_f$—$(CH_2)_n$—$S(O)_2$—$N(R^1)$—$C(R^5)(R^6)$—$C_mH_{2m}$—$]_2N^{\oplus}(R^4)_c(R^7)_d$ (Formula D);

wherein:
a and b are independently chosen from integers such that a≥0, b>0, and a+b=3, preferably b is 2 or 3;
c and d are independently chosen from integers such that c≥0, d>0, and c+d=2, preferably d is 2;
each $R_f$ is the same in i) and ii) and chosen from a $C_2$-$C_{12}$ polyfluoroalkyl, comprising partially of completely fluorinated linear or branched alkyl, optionally interrupted by one to four groups chosen from: —O—, —S—, —S(O)—, and —$S(O)_2$—;
each n in i) and ii) is the same and chosen from an integer from 0 to 6;
each m in i) and ii) is the same and chosen from an integer from 0 to 10;
each $R^1$, $R^5$, $R^6$ is independently chosen from hydrogen, $C_1$ to $C_6$ hydroxyalkyl, $C_1$ to $C_6$ halogen substituted alkyl, or a $C_1$ to $C_6$ linear or branched alkyl; provided that each $R^1$ in i) and ii) are the same, each $R^5$ in i) and ii) are the same, and each $R^6$ in i) and ii) are the same;
each $R^4$ in i) and ii) are the same and chosen from hydrogen or a $C_1$ to $C_6$ alkyl, or a $C_1$ to $C_6$ hydroxyalkyl;
each $R^7$ is independently chosen from a hydroxycarbonyl substituted $C_1$ to $C_6$ alkyl, such as —$CH_2$—C(O)—$O^-$, and oxysulfonylalkyl-, such as —$CH_2$—CH(OH)—$CH_2$—$S(O)_2$—$O^-$, and —$(CH_2)_3$—$S(O)_2$—$O^-$, their corresponding metal and ammonium salts, and mixtures thereof.

In another embodiment, the mixture of aminosulfonates and aminocarboxylates of the present invention is prepared from amines of Formulae A and B wherein $R_f$ is the same and chosen from $CF_3(CF_2)_5$, or $CF_3(CF_2)_3$; n is the same and is 2; each $R^1$ is the same and chosen from hydrogen, methyl or ethyl; $R^4$ is chosen from hydrogen, methyl or ethyl.

In yet another embodiment, the mixture of aminosulfonates and aminocarboxylates of the present invention is prepared from amines of Formulae A and B wherein each $R_f$ is the same and chosen from $CF_3(CF_2)_5$, or $CF_3(CF_2)_3$; each n is the same and is 2; each $R^1$, $R^4$, $R^5$ and $R^6$ is the same and is hydrogen; and each m is the same and is 2.

DETAILED DESCRIPTION OF THE INVENTION

Trademarks are shown herein in upper case.
The various reactions resulting in the formation of the desired aminosulfonates and aminocarboxylates (Formulae C & D) from the polyfluoroalkylsulfonamido alkyl amine mixture (Formulae A & B) of the invention may be represented as follows:

Reaction 1: Formation of the mixture of polyfluoroalkylsulfonamido alkyl amines of Formulae A and B

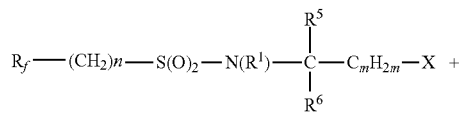

Formula 1:
polyfluoroalkylsulfonamido alkyl halide

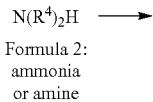

Formula 2:
ammonia or amine

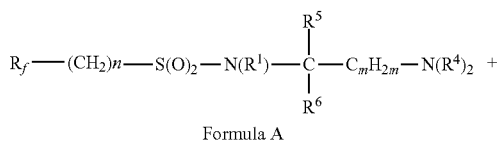

Formula A

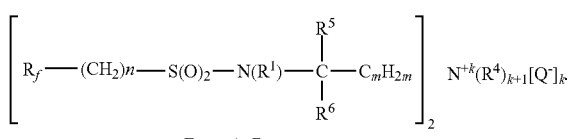

Formula B wherein X is a halogen selected from Cl, Br, I, and mixtures thereof.

In Formula 1, $R_f$ is chosen from a $C_2$-$C_{12}$ polyfluoroalkyl optionally interrupted by one to four groups chosen from: —O—, —S—, —S(O)—, and —S(O)$_2$—;

n is chosen from an integer from 0 to 6; $R^1$, $R^5$, $R^6$ are independently chosen from hydrogen, $C_1$ to $C_6$ hydroxyalkyl, $C_1$ to $C_6$ halogen substituted alkyl, or a $C_1$ to $C_6$ linear or branched alkyl;

$C_mH_{2m}$ is linear or branched alkyl, and m is chosen from an integer from 1 to 10; and X is a halogen selected from Cl, Br, I, and mixtures thereof. The substituents in Formulae A and B are as described above. In Formula 2, each $R^4$ is independently selected from hydrogen or a $C_1$ to $C_6$ alkyl, or a $C_1$ to $C_6$ hydroxyalkyl, preferably each $R^4$ is hydrogen thereby representing ammonia.

Reaction 2: Formation of polyfluoroalkylsulfonamido alkyl halide of Formula 1

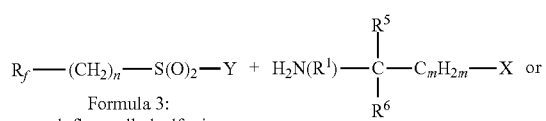

Formula 3:
polyfluoroalkylsulfonic compound

Formula 4A:
monoamino alkyl halide

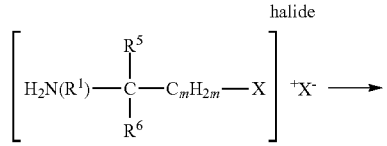

Formula 4B: salt of monoamino alkyl halide

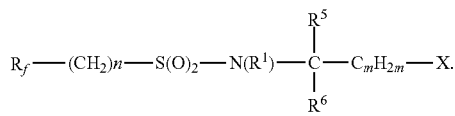

Formula 1 wherein Y is chosen from aryloxy, substituted aryloxy, or a halide such as F, Cl, or Br.

In Formulae 4A and 4B, $R^1$, $R^5$, $R^6$, and m are defined as above; and each X is a halogen independently chosen from Cl, Br, and I.

Reaction 3: Formation of polyfluoroalkylsulfonamido alkyl halide of Formula 1 by halo-de-hydroxylation of alcohols of Formula 5

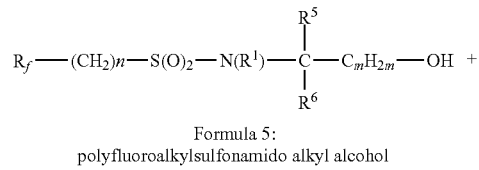

Formula 5:
polyfluoroalkylsulfonamido alkyl alcohol halogenating agent ⟶

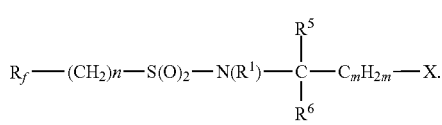

Formula 1

In Formula 5, $R_f$, n, $R^1$, $R^5$, $R^6$, and m are defined as above.

Reaction 4: Formation of polyfluoroalkylsulfonamido alkyl alcohol of Formula 5

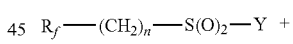

Formula 3

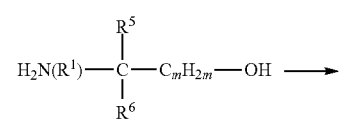

Formula 6:
amino alkyl alcohol

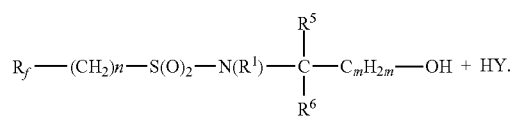

Formula 5

In Formula 6, $R^1$, $R^5$, $R^6$, and m are defined as above.

Reaction 5: Formation of the mixture of polyfluoroalkylsulfonamido alkyl aminosulfonates and aminocarboxylates of Formulae C and D

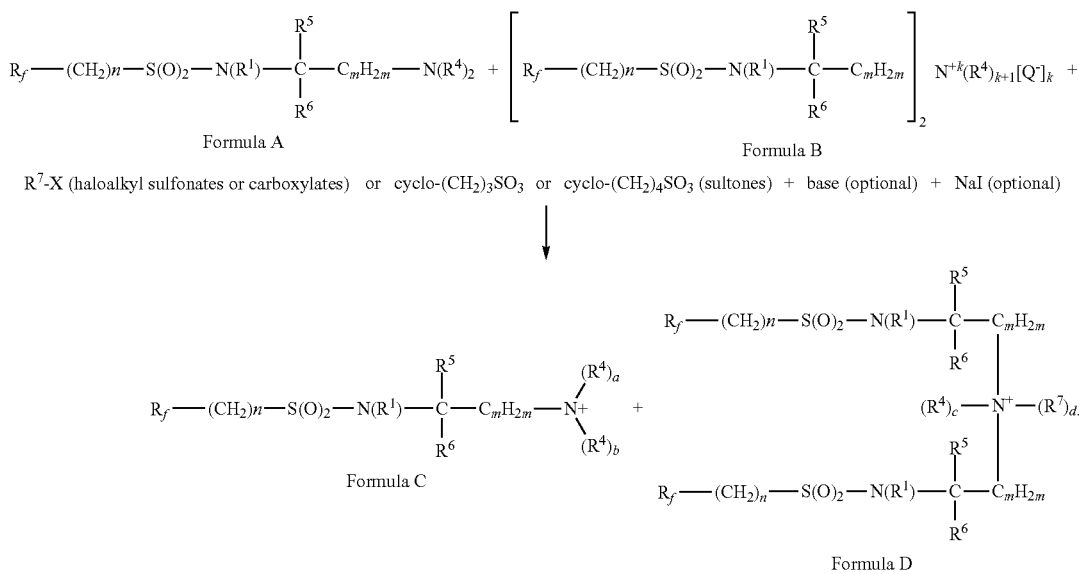

Formula A
Formula B
Formula C
Formula D wherein $R^7$ is as defined above and X is a halogen selected from Cl, Br, or I.

In preferred conditions of the Reaction 1, polyfluoroalkylsulfonamido alkyl halide of Formula 1 undergoes amino-de-halogenation with ammonia, producing polyfluoroalkylsulfonamido alkyl amine of Formula A, which upon further amino-de-halogenation reaction with alkyl halide of Formula 1 produces di(polyfluoroalkylsulfonamido alkyl) amine of Formula B. Therefore, polyfluoroalkylsulfonamido alkyl amines of Formulae A and B are both present in the product mixture. An example of the reaction conditions for subjecting a polyfluoroalkylsulfonamido alkyl halide (Formula 1) to amino-de-halogenation thereby producing a mixture of polyfluoroalkylsulfonamido alkyl amines (Formulae A and B) includes charging a reaction vessel with a polyfluoroalkylsulfonamido alkyl halide, and optionally an iodide salt catalyst, and solvent, which is then sealed, evacuated, and then charged with concentrated ammonia solution in water or methanol, preferably anhydrous ammonia, and heated to a reaction temperature of about 100 to 130° C., more preferably between 110 and 120° C. in a pressurized reactor. The pressure of the reactor is primarily determined by the partial pressure of ammonia at the reaction temperature and is about 70 to 600 psi. To maintain a high ratio (from about 10:1 to about 99:1) of amine of Formula A to amine of Formula B, a 10 to 200 fold molar excess of ammonia to polyfluoroalkylsulfonamido alkyl halide may be used; preferably a 25 to 150 molar excess, and more preferably a 50 to 100 molar excess. The reaction temperature is maintained for about 4 to 12 hours. The contents of the reactor are then cooled to about 20 to 25° C., and excess of ammonia is vented out. The unused ammonia can be scrubbed or condensed to recycle into the next reaction batch. The contents of the reactor are optionally filtered. A strong base (e.g., NaOH, KOH), preferably in powdered form, to convert the ammonium salts to a corresponding amines, and, optionally, activated carbon, to reduce the color of the mixture or final product, can then be added to the mixture of product, solvent and ammonium salts, allowed to stir, and filtered, to obtain the solution of the product. The solvent can then be evaporated from the filtrate with vacuum to obtain a solid product comprising typically 70 to 98 wt. % of a mixture of polyfluoroalkylsulfonamido alkyl amines (Formulae A and B).

Referring to Reaction 2, an example of the reaction conditions for forming a polyfluoroalkylsulfonamido alkyl halide of Formula 1 includes dissolving a monoamino alkyl halide or salt thereof (Formulae 4A or 4B) in a vessel (preferably under inert anhydrous conditions, e.g., with nitrogen purge) containing an appropriate aprotic solvent and additional base. The vessel is equipped with mechanical stirrer and a condenser. The contents of the vessel are heated to a temperature of about 10-20° C.; after which, a polyfluoroalkylsulfonic compound (Formula 3) is added to the vessel over a period of about 15 to 120 minutes while maintaining the temperature between about 10 to 50° C., more preferably between 20 and 40° C. The temperature can be controlled by means of the addition rate and external cooling. After addition of the polyfluoroalkylsulfonic compound, a reaction temperature is maintained at about 25 to 65° C. depending upon what additional base is used. After about 98 to 100 wt. % consumption of the polyfluoroalkylsulfonic acid halide (as measured by gas chromatography (GC) analysis), a strong acid (e.g., HCl or $H_3PO_4$) may be added to adjust the pH to about 2 to 7 (preferably 4 to 5) causing the conversion of unreacted monoamino alkyl halide of Formula 4A to a corresponding ammonium alkyl halide salts of Formula 4B, and conversion of additional base to its corresponding salts of these strong acids, which are removed by filtration. The filtrate can be further dried in vacuum to remove solvent and obtain solid product. Product or its solution in appropriate solvent can be optionally washed with water to remove traces of salts.

Referring to Reaction 3, an example of the reaction conditions for forming a polyfluoroalkylsulfonamido alkyl halide (Formula 1) by halo-de-hydroxylation of a polyfluoroalkylsulfonamido alkyl alcohol of (Formula 5) includes: charging a stirred vessel with polyfluoroalkylsulfonamido alkyl alcohol dissolved in an aprotic solvent; the addition of a halogenation agent; reacting the contents of the vessel at a temperatures determined by the reactivity of the halogenating agent, typically between about 40 to 130° C., for about 30 to 240 minutes; and removing solvent and excess halogenation agent by distillation, and, optionally, hydrolysis, and further aqueous washing, to obtain crude product. The crude product can be further purified by recrystallization, e.g., from hydrocarbon solvent such as hexane or heptane.

Referring to Reaction 4, an example of the reaction conditions for forming a polyfluoroalkylsulfonamido alkyl alcohol of Formula 5 includes dissolving an amino alkyl alcohol (Formula 6) preferably 2 to 2.3 equivalents based on the polyfluoroalkylsulfonic compound of Formula 3, in a vessel (preferably under inert anhydrous conditions, e.g., with nitrogen purge) containing an appropriate solvent such as, for example, methylene chloride, butyronitrile, 1,2-dimethoxyethane, 1,2-diethoxyethane, diethyl ether, tetrahydrofuran, ethyl acetate, toluene, and mixtures thereof. The vessel is equipped with mechanical stirrer and a condenser. The contents of the vessel are maintained at a temperature of about 10-20° C.; after which, a polyfluoroalkylsulfonic compound (Formula 3) is added to the vessel over a period of about 15 to 120 minutes while maintaining the temperature between about 10-50° C., more preferably between 20 and 40° C. The temperature can be controlled by means of the addition rate and external cooling. After addition of the polyfluoroalkylsulfonic compound, the reaction is maintained at a temperature of about 25 to 55° C. After about 99 to 100 wt. % consumption of the polyfluoroalkylsulfonic compound (as measured by gas chromatography (GC) analysis), a strong acid (e.g., HCl or $H_3PO_4$) is added to adjust the pH to about 2 to 7 (preferably 4 to 5) causing the neutralization of unreacted aminoalkylalcohol of Formula 6, to form additional amount of ammonium halide salts of aminoalkylalcohol by-products which have lower solubility in the reaction solvent and are removed by filtration. The filtrate solution can be further dried in vacuum to remove solvent and obtain solid product. Product or its solution in appropriate solvent can be optionally washed with water to remove traces of salts.

Referring to reaction 5, the aminosulfonates and aminocarboxylates of the present invention corresponding to Formula C and D can be made by subjecting the mixture of amines, comprising a polyfluoroalkylsulfonamido alkyl amines (Formula A) and its di(polyfluoroalkylsulfonamido alkyl) amine analog (Formula B), to N-alkylation with haloalkyl substituted reagents, or other N-alkylating reagents, such as sultones, comprising 1,3-propane sultone or 1,4-butane sultone, optionally in the presence of a base and/or iodide salts.

An example of the reaction conditions for forming a polyfluoroalkylsulfonamido alkyl aminosulfonates and aminocarboxylates of Formula C and D includes dissolving a mixture of polyfluoroalkylsulfonamido alkyl amines of Formula A and B, in a vessel in an appropriate alcohol solvent at about 65-80° C. The alcohol solvents are selected from but not limited to 2-propanol, 2-butanol, 1-methoxy-2-propanol, 2-methoxyethanol, propylene glycol, dipropylene glycol monomethyl ether, etc. The vessel is equipped with mechanical or magnetic stirrer and a condenser. After which, one or more haloalkyl substituted reagents, comprising $ClCH_2CH(OH)CH_2SO_3Na$-hydrate, $Cl(CH_2)_3SO_3Na$, sodium monochloroacetate, and optionally other iodide salt, such as sodium or potassium iodide, or tetraalkyl ammonium iodide or their solutions in water and other co-solvent, are added to the vessel while maintaining the temperature of about 70-85° C. After that the solution of sodium hydroxide or potassium hydroxide in water are added over a period of about 10 to 20 minutes, and the reaction is maintained at 83 to 120° C. After about 99 to 100 wt. % consumption of the polyfluoroalkylsulfonamido alkyl amine (as measured by gas chromatography (GC) analysis), the reaction mixture is cooled to about 20-40° C. and neutralized by the addition of HCl to adjust the pH to about 5 to 9, more preferably 6 to 8. The obtained solution can be further filtered. The product is further diluted to the desired concentration, or dried to remove the solvents and water to obtain solid product. Product or its solution in water and, optionally, other co-solvents, preferably alcohols, is further used as a surface-active agent.

The aminosulfonates and aminocarboxylates (Formulae C and D) derived from the polyfluoroalkylsulfonamido alkyl amine mixture (Formulae A and B) have excellent surface active properties and significantly reduce the surface tension of aqueous solutions at low concentrations. Uses include, but are not limited to, aqueous film forming foams, foaming, wetting, leveling, dispersing and as emulsifying agents. Preferably, the compounds of this invention are useful active ingredients in fire fighting agents.

The compounds of Formulae C and D are useful as surfactants and are capable of lowering surface tensions when added to aqueous media at low concentrations. As shown in the surface tension measurements below, these compounds are capable of lowering the surface tension of aqueous media to values less than about 19 milli-newtons per meter, preferably less than about 17 milli-newtons per meter, at a concentration of the surfactant in the medium of less than about 0.5% by weight, preferably about 0.3% by weight, and more preferably about 0.1% by weight, which are superior to values obtained when such compounds are derived from polyfluoroalkylsulfonamido alkyl amine without di(polyfluoroalkylsulfonamido alkyl) amine analog. These surfactants are characterized by their efficiency in lowering the surface tension at low concentrations by selective adsorption on the interface, which is determined by the amphiphilic nature of the surfactants.

The present invention further comprises a fire fighting agent comprising compounds of Formulae C and D of this invention as described above. The fire fighting agent typically further comprises water or a solvent. Preferred solvents are alcohols or glycols, for example ethanol or 1,2-propylene glycol. The fire fighting agent can also further comprise a hydrocarbon surfactant. Suitable hydrocarbon surfactants are available commercially. Examples include SIMULSOL SL8 available from Seppic, Paris La Defense, France; SULFETAL 4069 available from Zschimmer & Schwartz, Lahnstein, Germany; TRITON X100 available from Roche, Basil, Switzerland; and AMPHOTENSID GB2009 available from Zschimmer & Schwartz, Lahnstein, Germany.

The fire fighting agent is in the form of a liquid or foam. Fire fighting foam concentrates are compositions useful in extinguishing combustible liquid fires, particularly those caused by hydrocarbons and/or polar solvents. Fire fighting foams generate a water film over the fuel surface separating the flammable source from the flames, thus extinguishing the fire. After the fire is extinguished, the foams also suppress the flammable vapors from releasing, reducing the risk of burnback, or re-ignition of the flammable vapors. Typically at the time of use, the foam concentrates are diluted with water, usually municipal water or seawater, generally at a concentration about 6% by weight of the agent in the water. Other suitable concentrations used for extinguishing fires include solution of 1% and 3% by weight. Generally, the agent is agitated with water and a fire fighting foamed solution is formed prior to application. One mode of agitation is to pass the fire fighting agent and water solution through a fire hose nozzle where mechanical agitation takes place with incorporation of air, which generates an extinguishing foam used to combat combustible liquid fires. The foaming solution may contain other additives that assist in extinguishing fires such as FORAFAC 1268, commercially available from E. I. du Pont de Nemours and Company, Wilmington, Del.

The present invention further comprises a method of extinguishing a fire comprising contacting the fire with a composition containing a compound of Formulae C and D as described above. The compounds of Formulae C and D are typically applied to the fire as a dilution in water, one or more solvents, or mixtures thereof, at a concentration of from about 1% to about 6% by weight of a mixture of Formulae C and D. These compounds can be applied as a liquid or a foam. These compounds can also be mixed with one or more surfactants as discussed above prior to contacting with the fire. A mixture of compounds of Formulae C and D are contacted with the fire by using a conventional mechanical fire extinguisher, conventional hose with nozzle, or other known means. Typically the compounds are applied continuously until the fire is extinguished.

The present invention provides several advantages. The compounds of Formulae C and D are amphoteric and have excellent surfactant properties. The compounds of Formulae C and D are stable in typical fire fighting formulations without precipitating out of solution. Mixtures of compounds of Formulae C and D are useful as a fire fighting agents in the form of a liquid or foam. The mixture of compounds C and D is also useful to extinguish fires quickly and aids in suppressing re-ignition of the fire.

EXAMPLES

Example 1

Example of Reaction 1

$CF_3(CF_2)_5C_2H_4SO_2NH(CH_2)_3Cl+NH_3+NaI$ (or KI, $Bu_4NI$)+2-propanol+water (optional)→$CF_3(CF_2)_5$ $C_2H_4SO_2NH(CH_2)_3NH_2CF_3(CF_2)_5C_2H_4SO_2NH(CH_2)_3Cl$ (10 g, 0.02 mol), 2-propanol (30 g), potassium iodide (KI, 0.33 g, 0.002 mol) were charged to the 210 mL HASTEL-LOY-C shaker tube. The shaker tube was sealed, evacuated, and charged with $NH_3$ (gas, anhydrous, 29 g, 1.7 mol) and heated at 110° C. for 8 hours at 720 psi. The excess of $NH_3$ was vented. The product mixture was filtered at 60° C. The product filtrate was treated with solid NaOH powder, activated carbon and filtered. The solvent was evaporated in vacuum to obtain orange to brown solid containing $CF_3$ $(CF_2)_5C_2H_4SO_2NH(CH_2)_3NH_2$ (80%), $CF_3(CF_2)_5C_2$ $H_4SO_2NH_2$ (13%), and $[CF_3(CF_2)_5C_2H_4SO_2NH(CH_2)_3]_2$ NH (2-3%) by GC and NMR analyses. $C_6F_{13}C_2H_4$ $SO_2NHC_3H_6NH_2$: $^1H$ NMR (DMSO-$d_6$) δ 1.75 (p, 2H, $CH_2CH_2CH_2$, J=7 Hz), 2.59 (m, 2H), 2.81 (t, 2H, J=7.7 Hz), 3.05 (t, 2H, J=7.0 Hz), 3.44 (m, 2H). $^{13}C$ NMR (DMSO-$d_6$) δ 120-105 (m, 60), 42.84 (10), 39.73 (10), 37.13 (10), 29.45 (10), 25.52 (t, 10, $CH_2CF_2$, J=22.8 Hz).

Example 1

Example of Reaction 1

$CF_3(CF_2)_5C_2H_4SO_2NH(CH_2)_3Cl$ (61 g, 0.12 mol), 1-butanol (110 g), potassium iodide (NaI, 2.34 g, 0.0156 mol) were charged to the 1300 mL HASTELLOY-C shaker tube. The shaker tube was sealed, evacuated, and charged with $NH_3$ (gas, anhydrous, 144 g, 8.5 mol) and heated at 110° C. for 11 hours at 713 psi. The resulting product solution was filtered at 60° C., and solids washed with 20 g of 1-BuOH. The combined 1-BuOH solution was washed with 50 mL of 5% NaOH solution and 4 g of brine at 60° C. and phase separated. Solution of product in 1-BuOH (293 g) was evaporated and to obtain 49.2 g of brown solid containing $CF_3(CF_2)_5$ $C_2H_4SO_2NH(CH_2)_3NH_2$ (80%), $CF_3(CF_2)_5C_2H_4SO_2NH_2$ (8% by GC), and $[CF_3(CF_2)_5C_2H_4SO_2NH(CH_2)_3]_2NH$ (3%).

Example 2

Example of Reaction 2

This is an example showing Reaction 2 were wherein a polyfluoroalkylsulfonamido alkyl halide, $CF_3(CF_2)_5(CH_2)_2$ $SO_2NH(CH_2)_3Cl$, was formed by reacting a polyfluoroalkyl-sulfonic compound, $CF_3(CF_2)_5(CH_2)_2SO_2Cl$, with a monoamino alkyl halide salt, $[H_3N(CH_2)_3Cl]^+$ $Cl^-$ (3-chloropropylamine hydrochloride)

$CF_3(CF_2)_5(CH_2)_2SO_2Cl$ (10 g), 3-chloropropyl amine hydrochloride (4.1 g), and 1,2-dimethoxyethane (20 g) solvent were added to the round bottom flask equipped with mechanical stirring under nitrogen. Solution of triethylamine (4.5 g) in 1,2-dimethoxyethane (10 g) solvent was added dropwise during 30 min at 20-30° C. at 250 rpm. Stirred for 12 h after the addition is completed. The reaction was monitored by GC to ensure the complete conversion 1. The final reaction mixture with pH of about 5 was filtered from solids through 2 mm layer of CELITE 545. The solids were washed with 1,2-dimethoxyethane (7 g) and combined filtrate was evaporated in vacuum to obtain 11.0 g of $CF_3(CF_2)_5(CH_2)_2SO_2NH$ $(CH_2)_3Cl$. The product was additionally dissolved in hot toluene (8 g) and washed with 15.5 mL of 1% HCl aqueous solution to remove traces of $NH_2(CH_2)_3Cl$.

Example 3

Example of Reaction 3

Preparation of $CF_3(CF_2)_5(CH_2)_2SO_2NH(CH_2)_3Cl$ from $CF_3(CF_2)_5(CH_2)_2SO_2NH(CH_2)_3OH$ using thionyl chloride.

$CF_3(CF_2)_5CH_2CH_2SO_2NH(CH_2)_3OH$ (15 g, 31 mmol.) product of the Example 16 and 30 mL of 1,2-dimethoxy-ethane was heated to 40° C. to dissolve. Thionyl chloride (SOCl$_2$, 5.47 g, 46 mmol.) was added dropwise to this solution during 30 min, and the resulting mixture was stirred at 40° C. for another 30 min. K$_2$CO$_3$ (2.35 g) was added and stirred at 40° C. for 30 min. The solution was decanted and solvent removed on rotary evaporator to obtain 13 g of white solid product. GC/MS (m/z): 56 (3), 69 (6), 77 (6), 119 (4), 131 (4), 140 (5), 169 (4), 213 (2), 263 (4), 277 (3), 327 (6), 376 (8), 420 (2), 440 (100), 441 (10), 484 (2), 486 (1), 504 (0.5). $^1H$ NMR (CDCl$_3$) δ 2.03 (p, 2H, $CH_2CH_2CH_2$, J=6.4 Hz), 2.60 (tm, 2H, $CH_2CF_2$, J=17.5 Hz), 3.26 (m, 2H, $CH_2SO_2$), 3.32 (t, 2H, $CH_2N$, J=6.5 Hz), 3.62 (t, 2H, $CH_2Cl$, J=6.0 Hz), 4.88 (1H, broad s). $^{13}C$ NMR (CDCl$_3$) δ 125-105 (m, 6C), 43.15 (b, 1C), 41.38 (1C), 39.68 (1C), 32.45 (1C), 26.00 (t, 1C, $CH_2CF_2$, J=22.8 Hz).

Example 4

Example of Reaction 4

Preparation of $CF_3(CF_2)_5(CH_2)_2SO_2NH(CH_2)_3OH$ from $CF_3(CF_2)_5(CH_2)_2SO_2Cl$ and $H_2N(CH_2)_3OH$ (3-amino-1-propanol).

3-aminopropan-1-ol (68.2 g, 0.91 mol) and 1,2-dimethoxyethane (276 g) were placed in 1 Liter round bottom flask equipped with mechanical stirring under nitrogen. Solution of $CF_3(CF_2)_5(CH_2)_2SO_2Cl$ (200.1 g, 0.45 mol.), in 1,2-dimethoxyethane (121 g) was added dropwise during 2.5 hours at 20-40° C. while stirring at 350 rpm. The reaction mixture was stirred at 55° C. for 2 h after the addition is completed, and monitored by GC to ensure the complete conversion of $CF_3(CF_2)_5(CH_2)_2SO_2Cl$. The reaction mixture was acidified with H$_3$PO$_4$ (1.8 g) to pH=5.5, decanted and filtered from solids through a layer of CELITE 545. The solids were washed with 1,2-dimethoxyethane (2×50 g, 1×30 g), and combined filtrate was evaporated in vacuum to obtain 215.2 g of dried product, containing by GC analysis 86% of $CF_3(CF_2)_5CH_2CH_2SO_2NH(CH_2)_3OH$ and 6% of $CF_3(CF_2)_5(CH_2)_2SO_2NH(CH_2)_3Cl$. NMR ($CDCl_3$) δ 1.83 (p, 2H, $CH_2CH_2CH_2$, J=5.9 Hz), 2.64 (tm, 2H, $CH_2CF_2$, J=17.0 Hz), 3.27 (m, 2H, $CH_2SO_2$), 3.34 (m, 2H, $CH_2N$), 3.85 (t, 2H, $CH_2OH$, J=5.5 Hz), 4.95 (1H, broad s).

Example 5

This shows the synthesis of aminocarboxylates from a mixture of polyfluoroalkylsulfonamido alkyl amines made in accordance with the invention.

In this example the end product achieved in Example 1 which contained a mixture of polyfluoroalkylsulfonamido alkyl amines (1.5 g, including primary $CF_3(CF_2)_5C_2H_4SO_2NH(CH_2)_3NH_2$ and secondary $[CF_3(CF_2)_5C_2H_4SO_2NH(CH_2)_3]_2NH$ amines), deionized water (6 g), sodium monochloroacetate (0.86 g), and 2-propanol (4.5 g) were added into a 3 neck 100 ml round bottom flask equipped with magnetic stirrer, thermocouple, and reflux condenser. The mixture was heated to 85° C., and sodium hydroxide (0.31 g) dissolved in deionized water (3 g) was added over 5 minutes. The reaction was heated to reflux during 8 hours. The pH of the resulting mixture was adjusted with concentrated hydrochloric acid (0.14 g) to pH=6.5. The final resulting aminosulfonate mixture (solids 9.3%) was further diluted in water for surface tension measurements to make aqueous solutions of 0.3 wt. % and 0.1 wt. ° A).

Comparative Example A

A surfactant composition was made in accordance with Example 5 except that the starting primary amine $CF_3(CF_2)_5C_2H_4SO_2NH(CH_2)_3NH_2$ did not contain the secondary amine $[CF_3(CF_2)_5C_2H_4SO_2NH(CH_2)_3]_2NH$ analog, (solids 14.68%). This aminosulfonate (solids 9.3%) was further diluted in water for surface tension measurements to make aqueous solutions of 0.3 wt. ° A) and 0.1 wt. ° A).

Example 6

This shows the typical synthesis of aminosulfonates and aminocarboxylates from a mixture of polyfluoroalkylsulfonamido alkyl amines made in accordance with the invention.

In this example the end product achieved in Example 1 which contained a mixture of polyfluoroalkylsulfonamido alkyl amines (1.5 g, including primary $CF_3(CF_2)_5C_2H_4SO_2NH(CH_2)_3NH_2$ and secondary $[CF_3(CF_2)_5C_2H_4SO_2NH(CH_2)_3]_2NH$ amines, deionized water (6.0 g), $ClCH_2CH(OH)CH_2SO_3Na$-hydrate (0.91 g), sodium monochloroacetate (0.54 g), and 2-propanol (4.5 g) were added into a 3 neck 50 ml round bottom flask equipped with magnetic stirrer, thermocouple, and reflux condenser. The mixture was heated to 75-80° C. to dissolve the components, and sodium hydroxide (0.16 g) dissolved in deionized water (3.2 g) was added over 5-15 minutes. The reaction was heated to 83° C. during 10-18 hours until the complete consumption of the starting $CF_3(CF_2)_5C_2H_4SO_2NH(CH_2)_3NH_2$ is observed by GC. The pH of the resulting mixture was adjusted with concentrated hydrochloric acid (0.24 g) to pH=8. The final resulting aminosulfonate mixture was further dried in vacuum to obtain 2.2 g (solids 14.7 wt. %) and dissolved in deionized water to make 0.1 wt. % and 0.3 wt. % solutions and used after 24 h for surface tension measurements. No significant precipitate was observed upon cooling and storage for 24 h.

Comparative Example B

A surfactant composition was made in accordance with Example 6 except that the starting primary amine $CF_3(CF_2)_5C_2H_4SO_2NH(CH_2)_3NH_2$ did not contain the secondary amine $[CF_3(CF_2)_5C_2H_4SO_2NH(CH_2)_3]_2NH$ analog. The dried aminosulfonate product (solids 13.8 wt. %) was further dissolved upon heating at 0.3 wt. % and 0.1 wt. % to obtain aqueous solutions. After cooling to room temperature and standing for 24 h, significant amount of white sediment was observed and removed by decantation and the obtained solution was used for surface tension measurements.

Example 7

This shows the typical synthesis of mixed aminosulfonates and aminocarboxylates from a mixture of polyfluoroalkylsulfonamido alkyl amines made in accordance with the invention.

In this example the end product achieved in Example 1A which contained a mixture of polyfluoroalkylsulfonamido alkyl amines 3.0 g, including primary $CF_3(CF_2)_5C_2H_4SO_2NH(CH_2)_3NH_2$ and secondary $[CF_3(CF_2)_5C_2H_4SO_2NH(CH_2)_3]_2NH$ (3%) amines, $ClCH_2CH(OH)CH_2SO_3Na$-hydrate (1.82 g), $ClCH_2COONa$ (1.08 g), isopropanol (9 g), NaI (0.93 g), deionized water (12 g), is heated to 85° C. Solution of sodium hydroxide (0.625 g) in deionized water (6 g) is added during 30 min. The mixture is transferred to the Hastelloy-C shaker tube and heated at 115° C. for 12 hours. The pH of resulting product (29.4 g) was adjusted with diluted HCl to pH=8.0, and dried in vacuum. The product (solids 14.9 wt. %) was further dissolved upon heating to obtain aqueous solutions at 0.3 wt % and 0.1 wt %. After cooling to room temperature and standing for 24 h, the obtained solutions were used for surface tension measurements.

Comparative Example C

A surfactant composition was made in accordance with Example 7 except that the starting primary amine $CF_3(CF_2)_5C_2H_4SO_2NH(CH_2)_3NH_2$ did not contain the secondary amine $[CF_3(CF_2)_5C_2H_4SO_2NH(CH_2)_3]_2NH$ analog. The dried aminosulfonate product had 15.5 wt. % solids.

Surface Tension Measurements

Surface tensions measurements were conducted with Kruss Tensiometer Model K11-Mk2, available from KRUSS of Hamburg, Germany.

Surface tension measurements (mN/m) for solutions of the surfactants of Examples 5-7 and Comparative Examples A-C in deionized water are shown below.

|  | Active ingredient (%) | Surface tension (mN/m) |
|---|---|---|
| Example 5 | 0.3% | 17.0 |
|  | 0.1% | 19.2 |
| Comparative Example A | 0.3% | 20.4 |
|  | 0.1% | 24.4 |
| Example 6 | 0.3% | 16.5 |
|  | 0.1% | 18.1 |

-continued

| | Active ingredient (%) | Surface tension (mN/m) |
|---|---|---|
| Comparative Example B | 0.3% | 16.7 |
| | 0.1% | 18.5 |
| Example 7 | 0.3% | 19.0 |
| | 0.1% | 21.7 |
| Comparative Example C | 0.3% | 21.1 |
| | 0.1% | 27.0 |

As shown in the table above, the di(polyfluoroalkylsulfonamido alkyl) amine analog as used in Examples 5, 6 and 7 imparts superior surfactant properties as represented by lower surface tension in aminosulfonates and aminocarboxylates manufactured therefrom. Conversely, in Comparative Examples A, B, and C the use of a polyfluoroalkylsulfonamido alkyl amine without its di(polyfluoroalkylsulfonamido alkyl) amine analog results in poorer surfactant properties (represented by higher surface tension) in aminosulfonates and aminocarboxylates manufactured therefrom.

What is claimed is:

1. A mixture of aminosulfonate or aminocarboxylate compositions, or mixtures thereof, which comprises:
   i) at least one compound represented by

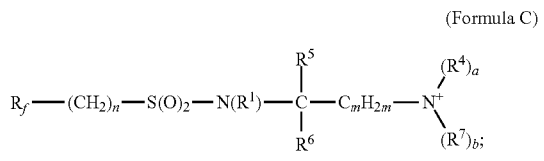
(Formula C)

and
   ii) at least one compound represented by

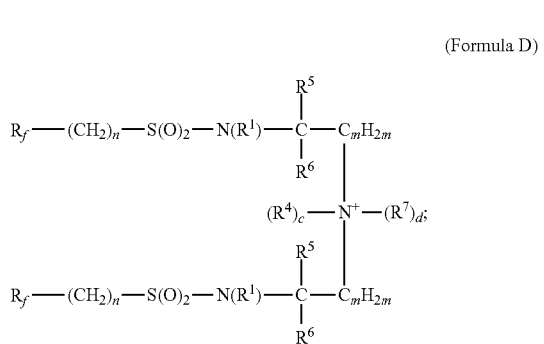
(Formula D)

wherein:
a and b are independently chosen from integers such that a≥0, b>0, and a+b=3;
c and d are independently chosen from integers such that c≥0, d>0, and c+d=2;
each $R_f$ is the same in i) and ii) and chosen from a $C_2$-$C_{12}$ polyfluoroalkyl, comprising partially or completely fluorinated linear or branched alkyl, optionally interrupted by one to four groups chosen from: —O—, —S—, —S(O)—, and —S(O)$_2$—;
each n in i) and ii) is the same and chosen from an integer from 0 to 6;
each m in i) and ii) is the same and chosen from an integer from 0 to 10;
each $R^1$, $R^5$, $R^6$ is independently chosen from hydrogen, $C_1$ to $C_6$ hydroxyalkyl, $C_1$ to $C_6$ halogen substituted alkyl, or a $C_1$ to $C_6$ linear or branched alkyl; provided that each $R^1$ in i) and ii) are the same, each $R^5$ in i) and ii) are the same, and each $R^6$ in i) and ii) are the same;
each $R^4$ in i) and ii) are the same and chosen from hydrogen or a $C_1$ to $C_6$ alkyl, or a $C_1$ to $C_6$ hydroxyalkyl;
each $R^7$ is independently chosen from a hydroxycarbonyl substituted $C_1$ to $C_6$ alkyl, and oxysulfonylalkyl, their corresponding metal and ammonium salts, and mixtures thereof.

2. A surfactant comprising the mixture of aminosulfonate or aminocarboxylate compositions, or mixtures thereof, of claim 1.

3. The mixture of claim 1 in the form of an aqueous film forming foam.

4. The mixture of claim 1 in the form of a fire fighting agent, wherein the fire fighting agent includes an aqueous film forming foam.

5. The mixture of claim 3 or claim 4 further comprising water or solvent or one or more surfactants.

6. A method of making a mixture of aminosulfonate or aminocarboxylate compositions, or mixtures thereof, of claim 1 comprising subjecting a mixture of amines including a polyfluoroalkylsulfonamido alkyl amine (Formula A) and a di(polyfluoroalkylsulfonamido alkyl) amine analog (Formula B) to N-alkylation with an N-alkylation reagent under suitable conditions to form the mixture of aminosulfonates or aminocarboxylates, or mixtures thereof, wherein the amines are represented by:
   i) at least one polyfluoroalkylsulfonamido alkyl amine represented by

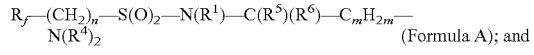
(Formula A); and ii) at least one di(polyfluoroalkylsulfonamido alkyl analog) of i) as represented by

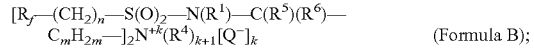
(Formula B);

wherein
Q is a monovalent anion;
k is 0 or 1;
each $R_f$ is the same in i) and ii) and chosen from a $C_2$-$C_{12}$ polyfluoroalkyl optionally interrupted by one to four groups chosen from: —O—, —S—, —S(O)—, and —S(O)$_2$—;
each n in i) and ii) is the same and chosen from an integer from 0 to 6;
each m in i) and ii) is the same and chosen from an integer from 0 to 10;
each $R^1$, $R^5$, $R^6$ is independently chosen from hydrogen, $C_1$ to $C_6$ hydroxyalkyl, $C_1$ to $C_6$ halogen substituted alkyl, or a $C_1$ to $C_6$ linear or branched alkyl; provided that each $R^1$ in i) and ii) are the same, each $R^5$ in i) and ii) are the same, and each $R^6$ in i) and ii) are the same;
each $R^4$ in i) and ii) are the same and chosen from hydrogen or a $C_1$ to $C_6$ alkyl, or a $C_1$ to $C_6$ hydroxyalkyl; and
the N-alkylating reagent is selected from 1,3-propane sultone or 1,4-butane sultone or the N-alkylating reagent is a haloalkyl substituted reagent selected from the group consisting of ClCH$_2$CH(OH)CH$_2$SO$_3$Na-hydrate, Cl(CH$_2$)$_3$SO$_3$Na and sodium monochloroacetate.

7. The method of claim 6, wherein the N-alkylation reaction occurs in the presence of a base selected from sodium hydroxide or potassium hydroxide.

8. The method of claim 7, further comprising an iodide salt selected from sodium iodide, potassium iodide or tetraalkyl ammonium iodide.

9. The method of claim 6, wherein the mixture of amines is prepared by subjecting a polyfluoroalkylsulfonamido alkyl halide to amino-dehalogenation with ammonia or an amine under suitable conditions to form a mixture of at least a polyfluoroalkylsulfonamido alkyl amine and at least a di(polyfluoroalkylsulfonamido alkyl) amine wherein:

i) the polyfluoroalkylsulfonamido alkyl halide is represented by $R_f$—$(CH_2)_n$—$S(O)_2$—$N(R^1)$—$C(R^5)(R^6)$—$C_mH_{2m}$—X (Formula 1); X is a halogen selected from Cl, Br, I and mixtures thereof; and ii) the ammonia or amine is represented by $N(R^4)_2H$ (Formula 2).

10. The method of claim 9, wherein the polyfluoroalkylsulfonamido alkyl halide (Formula 1) is prepared by reacting a polyfluoroalkylsulfonic compound with a monoamino alkyl halide, or salt thereof under suitable conditions to make a polyfluoroalkylsulfonamido alkyl halide wherein:

i) the polyfluoroalkylsulfonic compound is represented by

$R_f$—$(CH_2)_n$—$S(O)_2$—Y    (Formula 3)

wherein Y is chosen from aryloxy, substituted aryloxy, or a halide; and ii) the monoamino alkyl halide or salt thereof is represented by

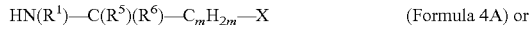

$HN(R^1)$—$C(R^5)(R^6)$—$C_mH_{2m}$—X    (Formula 4A) or

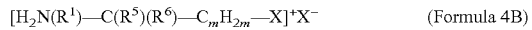

$[H_2N(R^1)$—$C(R^5)(R^6)$—$C_mH_{2m}$—$X]^+X^-$    (Formula 4B)

wherein each X is a halogen independently selected from Cl, Br, and I.

11. The method of claim 9, wherein the polyfluoroalkylsulfonamido alkyl halide (Formula 1) is prepared by reacting a polyfluoroalkylsulfonamido alkyl alcohol with a halogenating agent under suitable conditions to make a polyfluoroalkylsulfonamido alkyl halide wherein the polyfluoroalkylsulfonamido alkyl alcohol is represented by

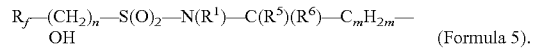

$R_f$—$(CH_2)_n$—$S(O)_2$—$N(R^1)$—$C(R^5)(R^6)$—$C_mH_{2m}$—OH    (Formula 5).

12. The method of claim 11, wherein the halogenating agent is selected from HCl, HBr, HI, $SOCl_2$, $SOBr_2$, $SOI_2$, $PCl_3$, $PBr_3$, or $PI_3$.

13. The method of claim 11, wherein the polyfluoroalkylsulfonamido alkyl alcohol (Formula 5) is prepared by reacting a polyfluoroalkylsulfonic compound with an amino alkyl alcohol under suitable conditions to make the polyfluoroalkylsulfonamido compound wherein:

i) the polyfluoroalkylsulfonic compound is represented by

$R_f$—$(CH_2)_n$—$S(O)_2$—Y    (Formula 3)

Y is chosen from aryloxy, substituted aryloxy, or a halide selected from F, Cl, or Br; and ii) the amino alkyl alcohol is represented by

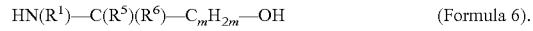

$HN(R^1)$—$C(R^5)(R^6)$—$C_mH_{2m}$—OH    (Formula 6).

14. A method of extinguishing a fire comprising contacting the fire with a composition containing the mixture of claim 1.

* * * * *